US008327841B2

(12) United States Patent
Bradley (10) Patent No.: US 8,327,841 B2
(45) Date of Patent: Dec. 11, 2012

(54) METHOD AND DEVICE FOR DETERMINING THE LOCATION OF SNORING (75) Inventor: Donald Carmon Bradley, Kanata (CA)

(73) Assignee: BRAEBON Medical Corporation, Ottawa, Ontario (CA)

( * ) Notice: Subject to any disclaimer, the term of this patent is extended or adjusted under 35 U.S.C. 154(b) by 1256 days.

(21) Appl. No.: 12/062,998

(22) Filed: Apr. 4, 2008

(65) Prior Publication Data
US 2008/0249428 A1 Oct. 9, 2008

Related U.S. Application Data (60) Provisional application No. 60/910,089, filed on Apr. 4, 2007.

(51) Int. Cl.
A62B 7/00 (2006.01)
A62B 9/00 (2006.01)
A62B 18/00 (2006.01)
A61F 5/56 (2006.01)
A61B 5/08 (2006.01)

(52) U.S. Cl. .................... 128/200.24; 128/848; 600/532
(58) Field of Classification Search .................. 128/846, 128/848, 858, 861, 862, 863, 200.24; 433/2, 433/6, 10, 11, 25, 140; 600/532
See application file for complete search history.

(56) References Cited

U.S. PATENT DOCUMENTS
7,054,228 B1  5/2006  Hickling

OTHER PUBLICATIONS
"Frequency of a beating heart". Printed on Dec. 29, 2011.*

Jan et al., "Sound Source Localization in Reverberant Environments using an Outlier Elimination Algorithm", Proc. ICSLP '96, vol. 3, Issue , Oct. 3-6, 1996, vol. 3, pp. 1321-1324.
Brandstein et al., "A Practical Time-Delay Estimator for Localizing Speech Sources with a Microphone Array", Computer speech & language (Comput. speech lang.) ISSN 0885-2308, Computer speech and language 1995, vol. 9, No. 2, (20 ref.) , Jun. 20, 1995, pp. 153-169.
Mast, "Empirical relationships between acoustic parameters in human soft tissues", Acoustics Research Letters Online, Oct. 2000, vol. 1, Issue 2, pp. 37-42.
Rose et al, "Validation of speed of sound for the assessment of cortical bone maturity", European Journal of Orthodontics 27 (2005), pp. 190-195.
Fix et al., "Acoustic analysis of snoring sound in patients with simple snoring and obstructive sleep apnoea", Eur Respir J, 1996, vol. 9, pp. 2365-2370.
Sola-Soler et al, "Pitch Analysis in Snoring Signals From Simple Snorers and Patients With Obstructive Sleep Apnea", Conference Proceedings Second Joint EMBS-BMES Conference, Oct. 23-26, 2002, pp. 1527-21528.

(Continued)

Primary Examiner — Frank W Lu
(74) Attorney, Agent, or Firm — Mukundan Chakrapani Borden Ladner Gervais LLP (57) ABSTRACT The treatment of snoring related sleep disorders require the knowledge of the location of origin of snoring in a patient. A method and device are provided for the determination of a location of origin of a primary vibration signal generated by snoring in an upper airway of a patient. At least two sensors are used to respectively detect the primary vibration signal and to generate respective intermediate signals. The sensors are spaced apart in a longitudinal direction of the patient's neck. The respective intermediate signals are processed to generate an output signal. The output signal is indicative of the location of origin.

10 Claims, 12 Drawing Sheets

OTHER PUBLICATIONS

Pasterkamp et al., "Posture-dependent change of tracheal sounds at standardized flows in patients with obstructive sleep apnea", Chest 1996; 110; pp. 1493-1498.

Beck at al, "The acoustic properties of snores", Eur Respir J, 1995, vol. 8, pp. 2120-2128.

Duckitt et al, "Automatic detection, segmentation and assessment of snoring", Physiol. Meas. 27 (2006) pp. 1047-1056.

* cited by examiner

Fig 1

(Prior Art)

Fig 2

(Prior Art)

Fig 3

(Prior Art)

Fig 4

(Prior Art)

METHOD AND DEVICE FOR DETERMINING THE LOCATION OF SNORING

CROSS-REFERENCE TO RELATED APPLICATIONS

The present application claims priority to U.S. Provisional Patent Application No. 60/910,089 filed on Apr. 4, 2007, the contents of which are expressly incorporated herein in their entirety.

FIELD OF THE INVENTION

The present invention relates generally to a device for determining the location of snoring.

BACKGROUND OF THE INVENTION

It is estimated that at least 45% of all adults snore occasionally and 25% are habitual snorers. Snoring may decrease a person's ability to have a good night's sleep creating conditions for daytime sleepiness. Snoring is a sign of upper airway resistance and is one of the precursor indicators to obstructive sleep apnea (OSA). OSA is a condition that affects an estimated 14 million Americans. The condition is caused by relaxation of the soft tissue in the upper airway during sleep, resulting in obstruction of the upper airway. The obstruction can occur in nasal passages, in the upper pharyngeal or in the lower pharyngeal areas. OSA is characterized by a complete cessation of breathing during sleep for 10 or more seconds (apnea), or a reduction in breathing for 10 or more seconds causing a 4% decrease in blood oxygen level (hypoapnea). Individuals having 5 or more apneic or hypoapneic events per hour are diagnosed as suffering from OSA. The obvious side effects of sleep apnea are daytime sleepiness and chronic fatigue. However, OSA is known to be a contributing factor in hypertension, heart disease, as well as other serious health conditions.

Figure 1:
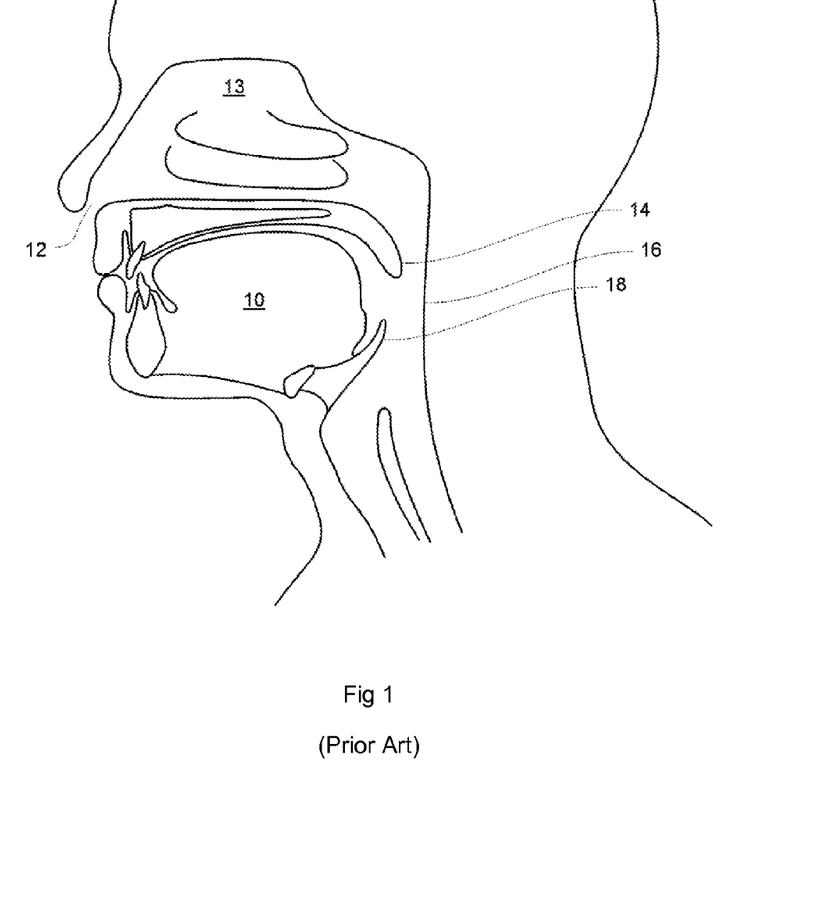
FIG. 1 is a longitudinal cross section of the human head and neck.
Figure 2:
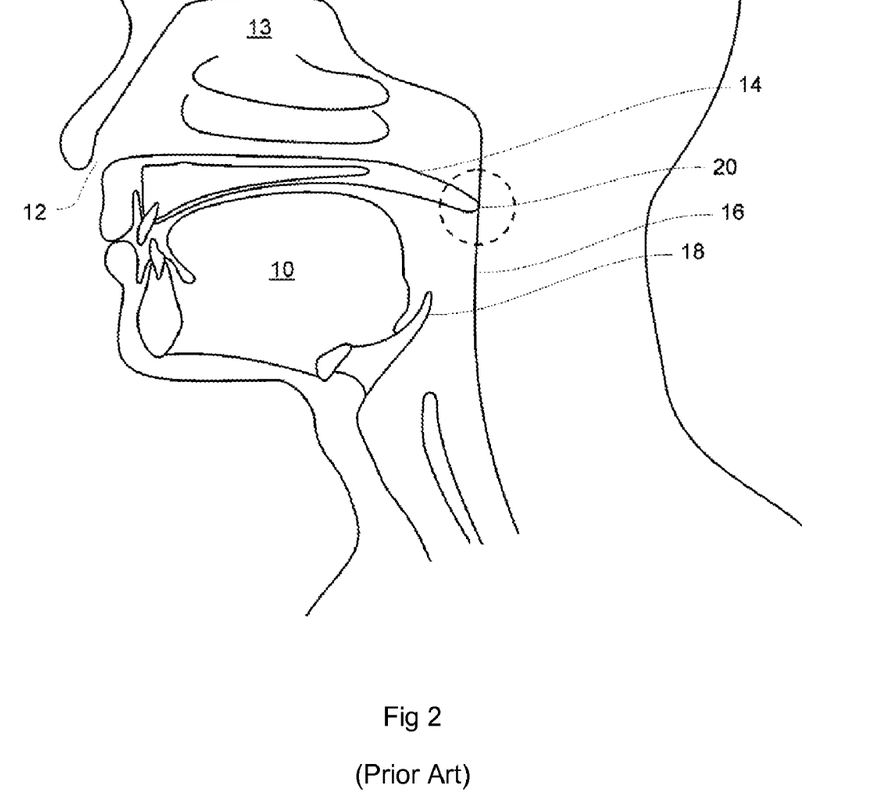
FIG. 2 is a longitudinal cross section of the human head and neck showing contact of the soft palette and uvula with the back of the throat.
Figure 3:
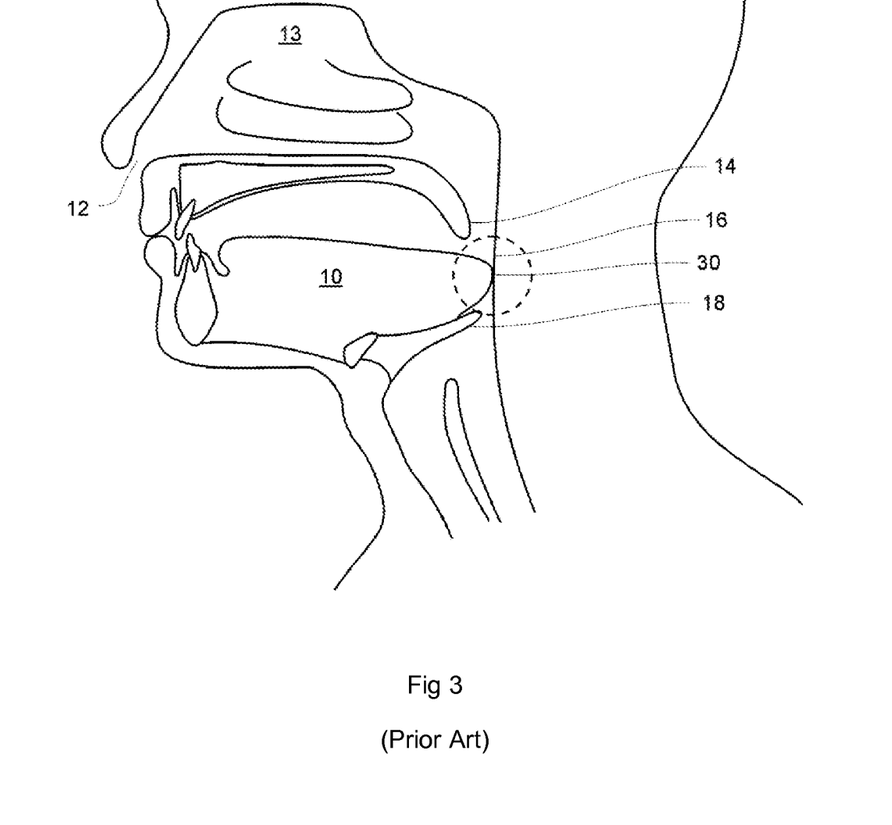
FIG. 3 is a longitudinal cross section of the human head and neck showing contact of the geneoglosial (tongue) with the back of the throat.
Figure 4:
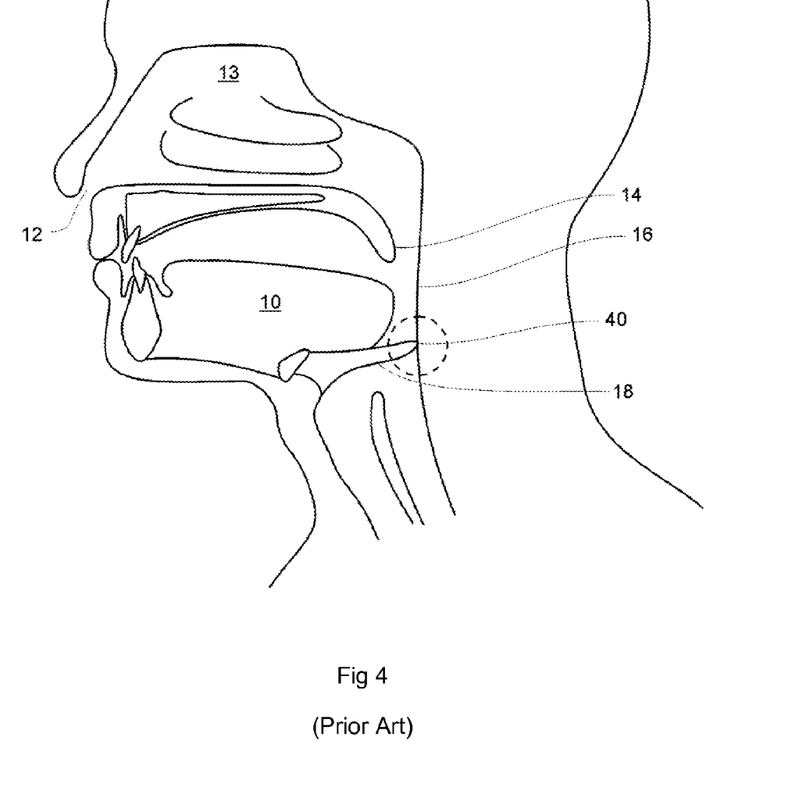
FIG. 4 is a longitudinal cross section of the human head and neck showing contact of the epiglottis with the back of the throat.

Snoring is defined as the sound made by vibrations of tissue in the upper airway corresponding to vibrations of obstructions in the nasal passages 13, the soft palate, the genioglossal muscle or the epiglottis, as shown in FIG. 1. This region is known as the upper airway and is defined as that portion of the respiratory tract beginning at the mouth and nose and ending at the larynx (voice box). These vibrations are caused by turbulence inside the airway during inspiration or expiration. The turbulence is caused by a partial blockage that may be located anywhere from the tip of the nose 12 to the vocal chords. Snoring vibrations can originate from the oropharynx soft palette 14 and other associated objects such as the tonsils and adenoids or making contact with the upper region of the back of the throat 20 as shown in FIG. 2, the base of the tongue 10 vibrating against the mid-region of the back of the throat 30 as shown in FIG. 3, or from the epiglottis 18 vibrating against the lower region of the back of the throat 40 as shown in FIG. 4. The back of the throat is generally designated by reference numeral 16 in FIGS. 1-4. The specific points of contact causing snoring in a patient are designated by reference numerals 20, 30 and 40 as discussed above.

Current diagnostic practices test for the presence of snoring and may go so far as to quantitatively measure the snoring intensity or frequency distribution and power spectrum of the snoring sound. During a polysomnogram (diagnostic sleep test) one of three sensing devices are used. A microphone may be used to pick up the auditory snoring signal. This sensor suffers from artifacts, as it is able to pickup many other sounds other than snoring. A vibratory snoring sensor may be used to measure the vibration caused by snoring. This sensor is designed to pickup any vibration that occurs on the neck and as such will typically have movement and heart beat artifacts embedded within the signal. The third sensing device is a nasal pressure cannula. This device will measure the variations in the airflow signal that are assumed to be due to snoring. This sensor only functions if the pressure wave due to the vibration proceeds either out the nasal passage or oral passage and that the cannula captures enough of the pressure wave to register on the sensor element. Each one of these sensor devices is designed to output a signal based on whether there is snoring or not.

SUMMARY OF THE INVENTION

According to an aspect of the invention, there is provided a method for determining a location of origin of a primary vibration signal generated by snoring in an upper airway of a patient. The method comprises placing at least two sensors to respectively detect the primary vibration signal and to generate respective intermediate signals. The sensors are spaced apart in a longitudinal direction of the patient's neck. The respective intermediate signals are processed to generate an output signal. The output signal is indicative of the location of origin.

According to another aspect of the invention, there is provided a device for determining a location of origin of a primary vibration signal generated by snoring in an upper airway of a patient. The device comprises at least two sensors to respectively detect the primary vibration signal and to generate respective intermediate signals. A microprocessor receives the respective intermediate signals and generates an output signal indicative of the location of origin.

BRIEF DESCRIPTION OF THE DRAWINGS

Embodiments of the present invention will now be described, by way of example only, with reference to the attached Figures, wherein.

DETAILED DESCRIPTION

Currently, there are several treatments for snoring and sleep apnea. Patients suffering from snoring or sleep apnea may go through several modalities of treatments until they find one that works. Treatments for snoring and sleep apnea consist of constant positive airway pressure (CPAP) where air is pressurized inside the upper airway creating a pneumatic splint that reduces the chances of the airway collapsing during inhalation; nasal dilators to keep the nasal passage from collapsing during inspiration; surgery to remove tonsils and adenoids to open up the airway passage; surgery to reduce the uvula and or soft palate to stop the soft palate and uvula from creating an obstruction during inspiration; surgery to repair a deviated septum or surgery to clean up the nasal sinuses to allow more air to flow through the nasal passages thus reducing the chances of the patient mouth breathing which has been shown to cause snoring; and surgery to stiffen the soft palate reducing snoring, and mandibular advancement to stop the tongue from vibrating. However, for effective treatment, each one of these solutions depends on the location of the obstruction and the tolerance of the patient.

As an example, mandibular advancement or nasal dilators will most likely not cure snoring originating from the collapsing of the uvula or soft palate. Similarly, reducing surgery on the tonsils, adenoids, uvula or soft palate will most likely not cure snoring originating from the collapsing of the tongue, but mandibular advancement devices may cure this condition. Furthermore, nasal dilators, surgery on the nasal passages, reducing surgery on the tonsils, adenoids, uvula or soft palate will not cure snoring originating from the collapsing of the epiglottis. Therefore, knowledge of where the obstruction is located will greatly aid in the determination of the type of therapy that can be used.

Attempts are underway to determine if spectral analysis of the snoring sound can be used to reliably determine the location of the snoring. However, spectral analysis is complex and computation intensive.

Figure 5:
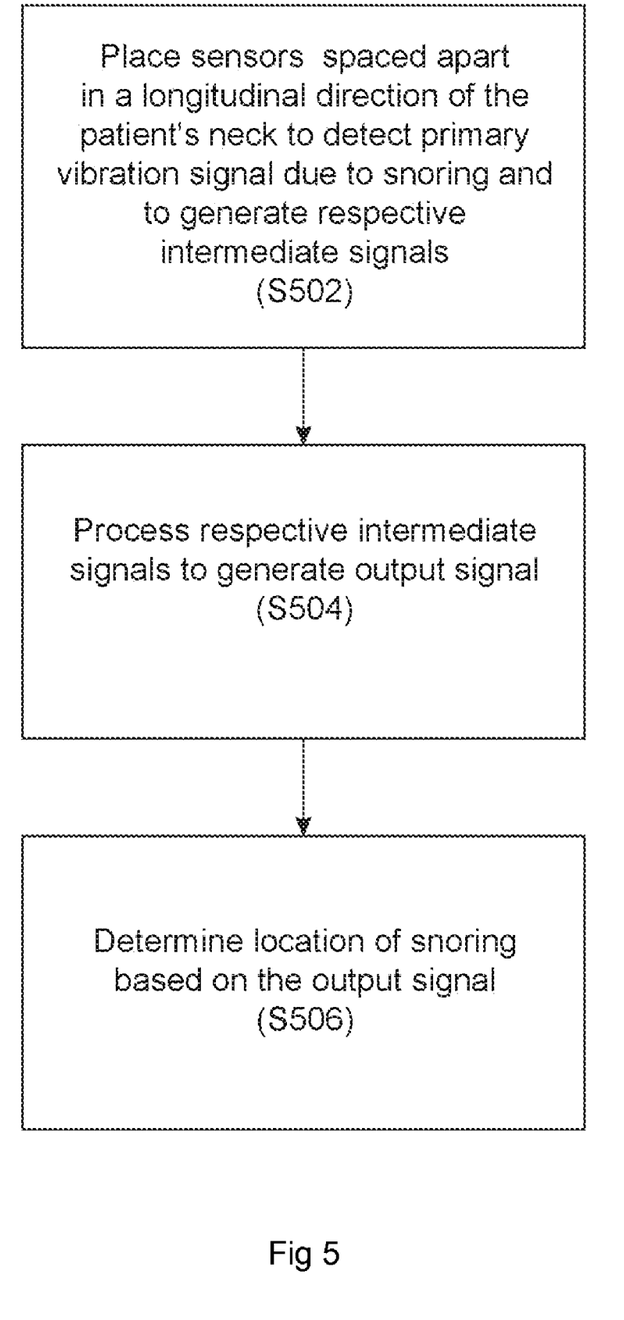
FIG. 5 is a flow diagram of a method for determination of a location of snoring in an upper airway of a patient in accordance with an embodiment.

Generally, there is provided a method for determining a location of origin of a primary vibration signal generated by snoring in an upper airway of a patient as shown in FIG. 5. The method comprises placing at least two sensors to respectively detect the primary vibration signal and to generate respective intermediate signals. The sensors are spaced apart in a longitudinal direction of the patient's neck (step S502). The respective intermediate signals are processed to generate an output signal (step S504). The location of origin of the primary vibration signal generated by snoring in the upper airway of the patient is then determined based on the output signal (step S506).

Figure 6:
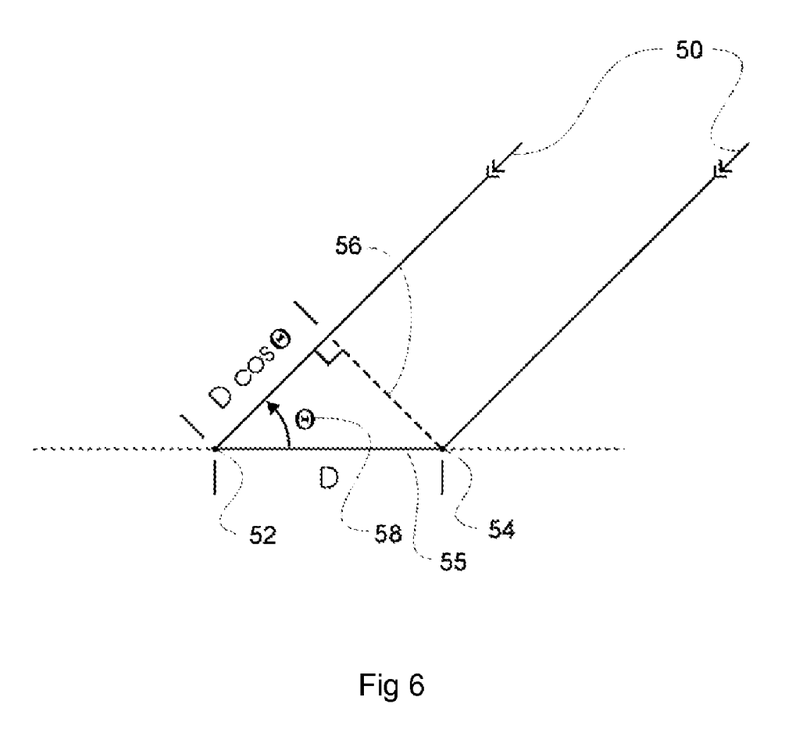
FIG. 6 is a ray diagram showing the path of the vibration signals and the associated calculation used in determining the angle of incidence in accordance with an embodiment.

In accordance with an embodiment, as shown in FIG. 6, vibrations originating in the upper airway of a patient are detected using two vibratory sensors 52 and 54 located a distance D 55 between each other in a longitudinal direction along the neck of the patient. In the exemplary embodiment shown in FIG. 6, the sensors are placed spaced apart in a straight line parallel to longitudinal direction of the patient's neck. However, the sensors may be placed spaced apart, offset and staggered from a straight line parallel to the longitudinal direction of the patient's neck, anywhere in the vicinity of the patient's neck. The vibratory sensors may be a microphone, accelerometer, piezo sensor, strain gauge, distortion sensor or any sensor that can measure either quantitatively or qualitatively a vibration, distortion or change in the physical dimensions of a surface while being located on the surface of an object.

The respective intermediate signals can be processed by selecting a characteristic of the respective intermediate signals that varies with the location of origin and by comparing the selected characteristic to generate the output signal. The selected characteristic can be, for example, the amplitude of vibration or an inflection in the signal and the time that the inflection occurred.

The output signal can be a time differential signal based on the detection time of the primary vibration signal at each of the at least two sensors. The determination of the location of origin comprises determining an angle of incidence of the primary vibration signals. The processing of the respective intermediate signals can include conditioning the respective intermediate signals for reducing electrical noise and limiting the respective intermediate signals to a pre-determined frequency range. The frequency range is set such that movement artifacts are removed. The inflections are compared to remove pulse artifacts by ignoring inflections that occur with a period of less than 2 s. Additionally, the processing can include determining a peak occurrence in the respective intermediate signals and comparing the peak occurrence in the respective intermediate signals for generating the output signal.

In a further embodiment, the primary vibration signal can be correlated to an independent secondary vibration signal indicative of snoring by the patient. The independent secondary vibration signal can be a filtered pressure wave generated by a nasal pressure cannula or a vibration signal generated by a snoring microphone.

In the following description, it is assumed that the vibration is located sufficiently further away and that the distance that the two vibratory sensors 52 and 54 are placed is small such that the incident primary vibration signals 50 are parallel at each sensor.

FIG. 6 shows the incident primary vibration signal 50 originating from a single source location. The incident primary vibration signal is first detected by the vibration sensor 54 and then at a later time by the vibration sensor 52. The difference in the distances traveled by the wave to the second vibratory sensor 52 is given by the following equation:

$$d = v \times t$$

where d is the additional distance traveled by the primary vibration signal detected at the vibration sensor 52, v is the velocity of the primary vibration signal in tissue and t is the time from the detection of the primary vibration signal at the vibration sensor 54 to the detection of the primary vibration signal at the vibration sensor 52. The velocity of the primary vibration signal in tissue is determined as described in the European Journal of Orthodontics 27 (2005) 190-195, E. C. Rose, et al, Validation of speed of sound for the assessment of cortical bone maturity. Based on this determination, the mean velocity is found to be 1.561 mm/µs with a standard deviation of 3.2% due to the difference in densities of specific types of tissue.

The additional distance travelled by the primary vibration signal to reach the vibration sensor 52 is obtained by drawing a line 56 that is perpendicular to the incident primary vibration signal at the vibration sensor 52 to the location of the vibration sensor 54. Thus, a right angled triangle is formed as shown in FIG. 6, from which the additional distance traveled can be calculated using the equation:

$$d = D \times \cos \Theta$$

where d is the additional distance travelled, D is the distance 55 between the two sensors and Θ is the angle of incidence 58.

Combining the above two equations and rearranging, the angle of incidence Θ is calculated using the equation:

$$\Theta = \cos^{-1}\left(\frac{v \times t}{D}\right)$$

Figure 7:
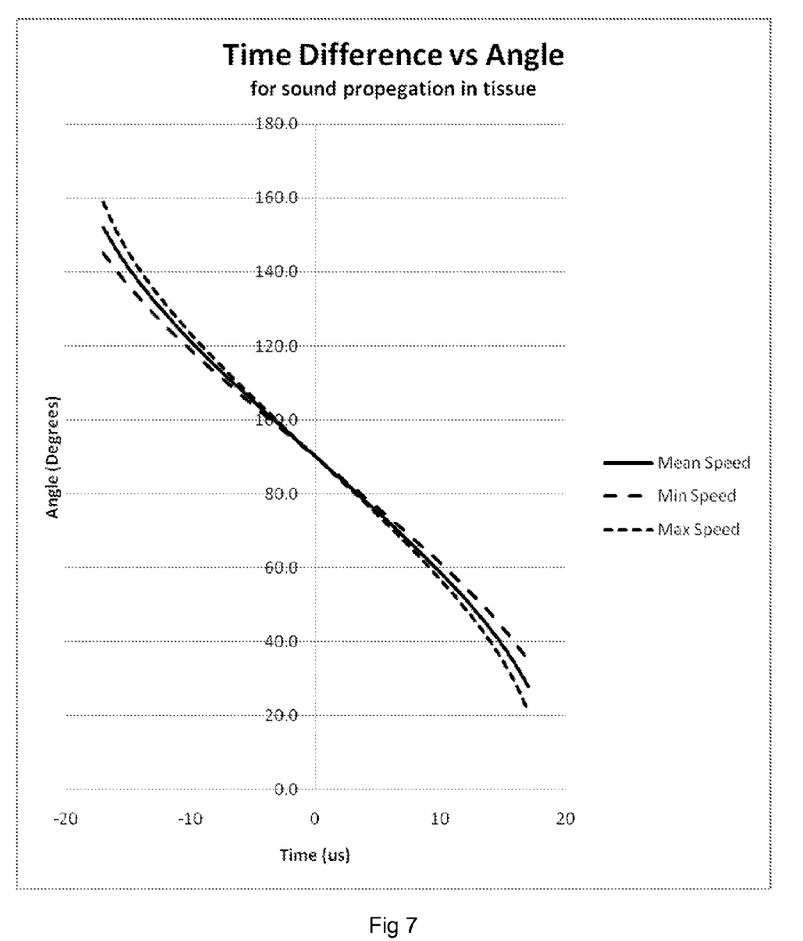
FIG. 7 is a graph of the time difference in sensing the vibrator signal and the angle of incidence of the vibration signal for propagation in various tissues in accordance with an embodiment.
Figure 8:
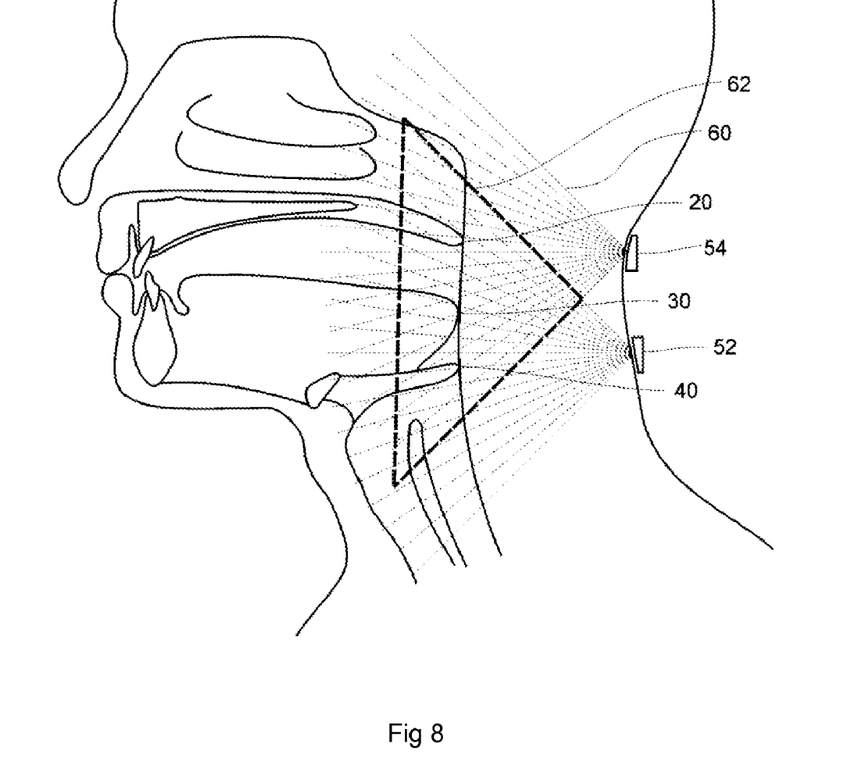
FIG. 8 is a ray diagram showing area of coverage of a sensor arrangement in accordance with an embodiment.

FIG. 7 shows the application of this equation using a constant value for D, the maximum, minimum and mean velocities for propagating signals in tissue over time vs. the calculated angle. From the graph shown in FIG. 6, the mean wave velocity and angle of incidence are directly proportional (yield a substantially straight line) to each other when the angle of incidence is in the range of 45° and 135°. Using this approximation on the allowed angles of incidence, the range of accurate localization is determined to be within the triangle 62 as shown in FIG. 8.

Figure 9:
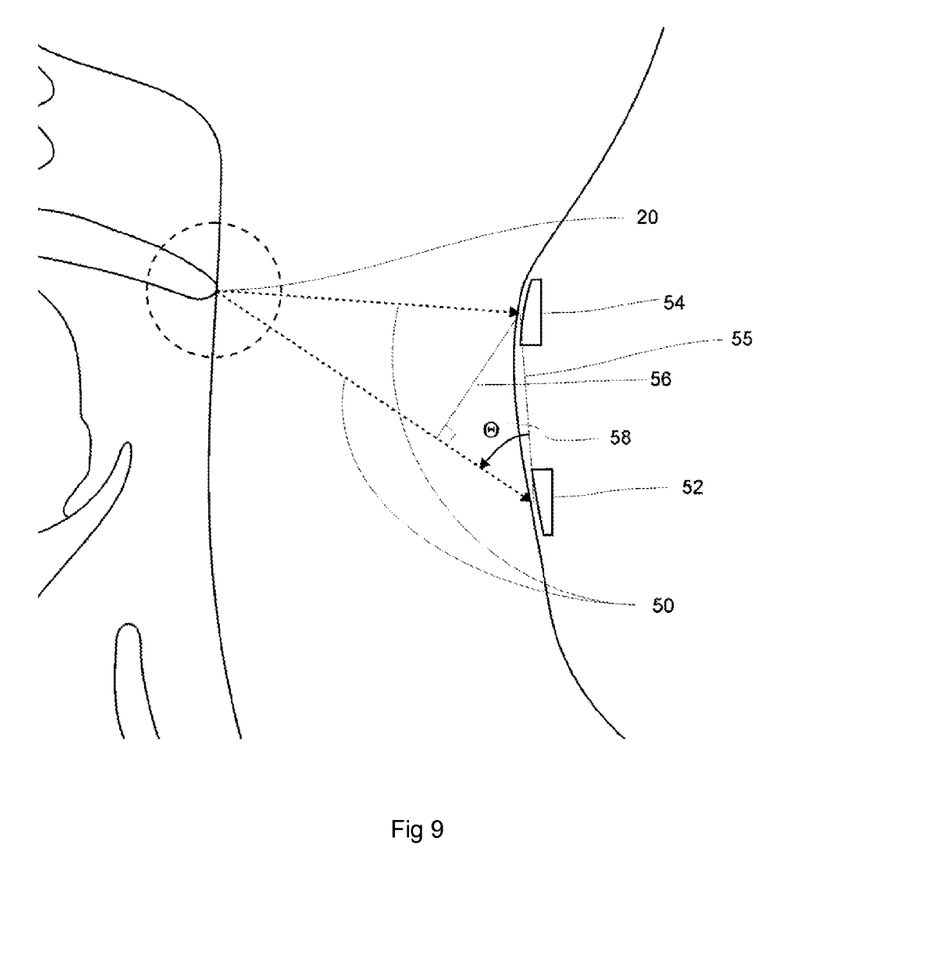
FIG. 9 is a ray diagram showing the path of the vibration signals being generated by the contact of the soft palette with the back of the throat.
Figure 10:
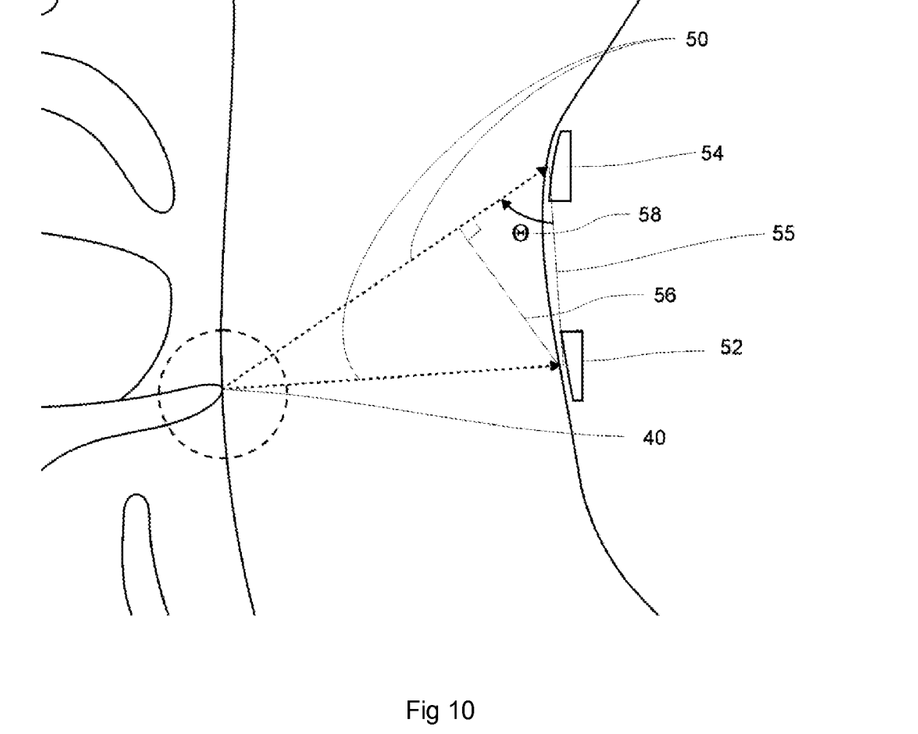
FIG. 10 is a ray diagram showing the path of the vibration signals being generated by the contact of the epiglottis with the back of the throat.

FIG. 9 and FIG. 10 are ray diagrams showing the path of the primary vibration signals being generated by the contact of the soft palette with the back of the throat 20 and by the contact of the epiglottis with the back of the throat 40, respectively. It is evident that the primary vibration signal is first detected at the vibration sensor 54 when the primary vibration signal is generated by the contact of the soft palette with the back of the throat (FIG. 9). On the other hand, when the primary vibration signal is generated by the contact of the epiglottis with the back of the throat, the primary vibration signal is first detected at the vibration sensor 52.

Figure 11:
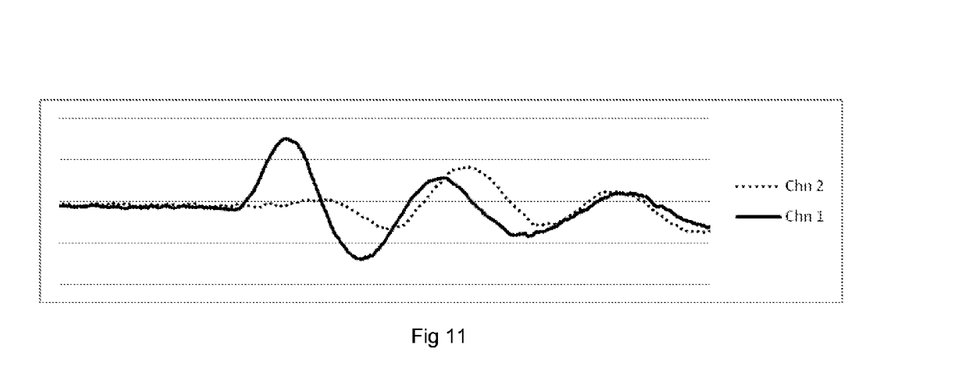
FIG. 11 is a graph of the signal being received from 2 piezo/vibratory sensors during a vibratory event located at an angle indicating the upper pharyngeal area or soft palette in accordance with an embodiment.

In an exemplary use of an embodiment, a vibration was induced simulating the location of snoring in the upper pharyngeal region, corresponding to FIG. 9. FIG. 11 shows a voltage vs. time graph of the primary vibration signal detected by two vibration sensors placed 2 cm apart. It is evident that the primary vibration signal is detected at sensor 1 (Chn1) before being detected at sensor 2 (Chn2). Thus, knowing the sound propagation time in a medium together with the distance between the sensors and the measured time difference, the angle of the location of where the snoring originated can be determined.

Figure 12:
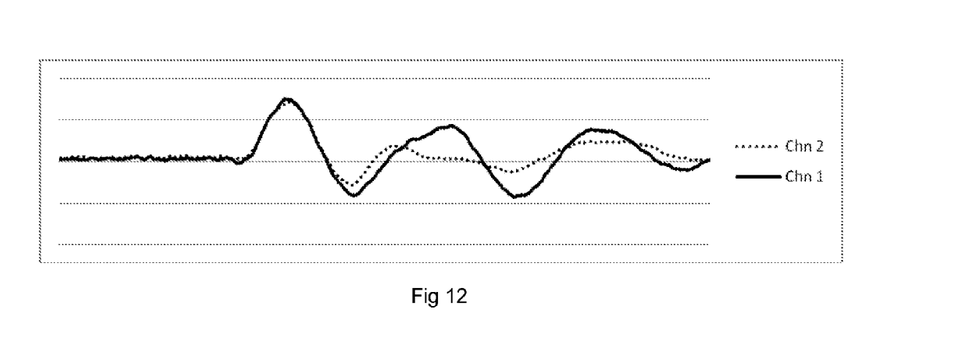
FIG. 12 is a graph of the signal being received from 2 piezo/vibratory sensors during a vibratory event located at an angle indicating the vibration of the tongue in accordance with an embodiment.

Similarly, FIG. 12 shows a voltage vs. time graph of the signal generated by two vibratory sensors placed 2 cm apart in the case where the vibration was induced simulating the location of snoring to be perpendicular from the midpoint of a straight line drawn between the two sensors. It is evident that the primary vibration signal is detected at sensor 1 and sensor 2 at the same time. In this case, the equation for the angle of incidence then becomes:

$$\Theta = \cos^{-1}\left(\frac{v \times 0}{D}\right)$$

which is easily calculated such that Θ=90 degrees.

Figure 13:
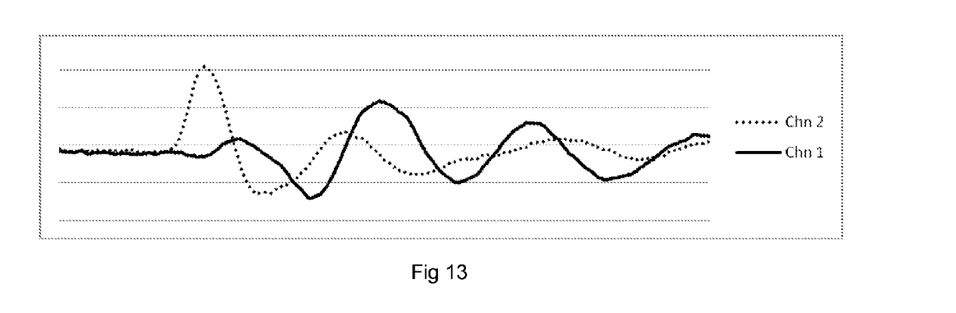
FIG. 13 is a graph of the signal being received from 2 piezo/vibratory sensors during a vibratory event located at an angle indicating vibration of the tongue or epiglottis in accordance with an embodiment; and, FIG. 14 is a block diagram of the controller for the determination of the location of snoring in accordance with an embodiment.

FIG. 13 shows a voltage vs. time graph of the signal generated by two vibratory sensors placed 2 cm apart in the case where the vibration was induced simulating the location of snoring in the lower pharyngeal region, corresponding to FIG. 10. It is evident that the primary vibration signal is detected at sensor 2 (Chn2) before sensor 1 (Chn1). Thus, knowing the sound propagation time in a medium together with the distance the sensors are apart and the measured time difference, the angle of the location of where the snoring originated can be determined.

In an embodiment, there is provided a device for determining a location of origin of a primary vibration signal generated by snoring in an upper airway of a patient. The device comprises at least two sensors to respectively detect the primary vibration signal and to generate respective intermediate signals. A microprocessor receives the respective intermediate signals and generates an output signal indicative of the location of origin of the primary vibration signal generated by snoring in the upper airway of the patient.

The device further comprises a signal-conditioning unit for reducing electrical noise and limiting the respective intermediate signals to a pre-determined frequency range. In an exemplary embodiment, the pre-determined frequency range is 20 to 1000 Hz. The device further comprises an analog to digital converter for converting the respective intermediate signals to corresponding respective digital signals for further processing by the microprocessor; and a digital to analog converter for converting the output signal of the microprocessor to a corresponding output analog signal indicative of the location of snoring in the upper airway of the patient. In exemplary embodiments, the sensors are vibration sensors and can be a microphone, accelerometer, a piezo sensor, a strain gauge, or a distortion sensor.

Figure 14:
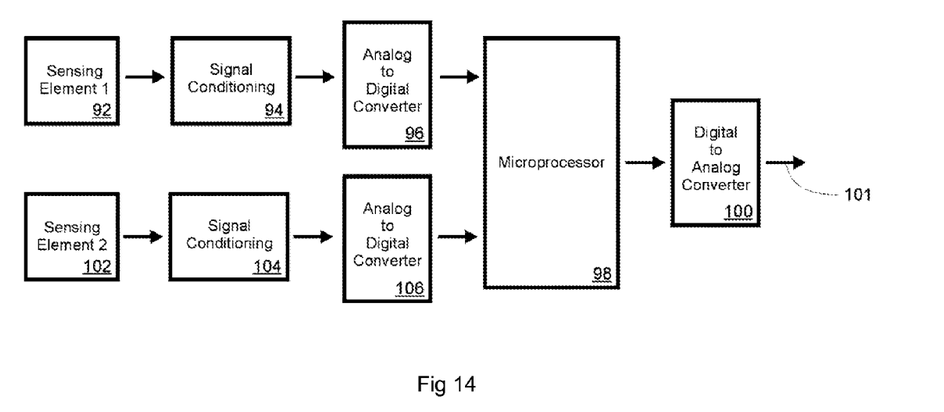

FIG. 14 is a block diagram of the various components of the device according to an embodiment. The sensors 92 and 102 are typically mounted spaced apart in longitudinal direction of the patient's neck. The first 92 and second 102 vibration sensors are connected to the processing unit. Each primary vibration signal, generated by snoring by the patient and detected by the vibration sensor is presented as a respective intermediate signal to the signal condition units 94 and 104. The signal condition units reduce electrical noise and only allow through selected frequencies, for example, in the 20 Hz to 1000 Hz range. The outputs from the signal conditioning units are then digitized by a hi-speed analog to digital converter 96 and 106. The digital output from the analog to digital converters are then sent to the microprocessor 98. The microprocessor filters the signals to remove any artifacts such as movement and pulse waveforms. The processing of the signal within the microprocessor unit is setup such that all the signals used in determining the location of the snoring are synchronized. The microprocessor performs a peak detection comparison on the two incoming intermediate vibration signals. The time difference between the two peaks are used to calculate the angle of incidence and a signal corresponding to this angle is sent to the digital to analog convertor 100 to output the corresponding signal. The output signal 101 is indicative of the location of snoring in the upper airway of the patient and may be in the form a DC voltage output, an oscilloscope output and any other suitable visual indicator. For continuous patient monitoring and testing, the output signal is remains constant for about 1 s and then resets for the next event.

To aid in the detection of snoring signal, the processing unit can use an independent secondary vibration signal indicative of snoring by the patient. The independent secondary vibration signal can be a filtered pressure wave generated by a nasal pressure cannula or a vibration signal generated by a snoring microphone.

In additional embodiments, the sensors can be mounted on a side of the patient's neck. In this embodiment, the primary vibration signal does not pass through the spine, thereby eliminating any distortion to the primary vibration signal due to transmission through bone.

Addition of a third sensor can further help in the precise location of the origin of the snoring signal. As described earlier, the types of therapy to be used for the treatment of snoring related sleep disorders require the differentiation between vibrations being located in the nasal passages and upper pharyngeal regions or vibrations being located in the lower pharyngeal regions. The use of only two vibratory sensors is sufficient for the localization of the origin of the snoring signal. Additional sensors yield more specific information regarding location. However, more sensors could be used as a backup to validate the results obtained from the first two sensors.

Embodiments of the invention can be represented as a software product stored in a machine-readable medium (also referred to as a computer-readable medium, a processor-readable medium, or a computer usable medium having a computer-readable program code embodied therein). The machine-readable medium can be any suitable tangible medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the invention. Those of ordinary skill in the art will appreciate that other instructions and operations necessary to implement the described invention can also be stored on the machine-readable medium. Software running from the machine-readable medium can interface with circuitry to perform the described tasks.

The above-described embodiments of the invention are intended to be examples only. Alterations, modifications and variations can be effected to the particular embodiments by those of skill in the art without departing from the scope of the invention, which is defined solely by the claims appended hereto.

What is claimed is:

1. A method for determining a location of origin of a primary vibration signal generated by snoring in an upper airway of a human patient, the method comprising:
   placing at least two vibratory sensors spaced apart along a longitudinal direction of the human patient's neck to detect the primary vibration signal;
   generating respective intermediate signals from the at least two vibratory sensors, the respective intermediate signals being within a pre-determined frequency range, the pre-determined frequency range being 20 to 1000 Hz;
   processing the respective intermediate signals by comparing times at which the primary vibration signal is detected by the at least two vibratory sensors thereby generating an output signal; and
   determining the location of origin of said primary vibration signal generated by snoring in said upper airway of said human patient based on the output signal.

2. The method of claim 1, wherein said processing the respective intermediate signals comprises:
   selecting at least one characteristic of the respective intermediate signals from a plurality of characteristics of the respective intermediate signals that vary with the location of origin.

3. The method of claim 1, wherein the output signal is a time differential signal based on the times at which the primary vibration signal is detected by the at least two vibratory sensors.

4. The method of claim 1, wherein said determining the location of origin of said primary vibration signal generated by snoring in said upper airway of said human patient comprises determining an angle of incidence of the primary vibration signals.

5. The method of claim 1, wherein said processing the respective intermediate signals comprises conditioning the respective intermediate signals to reduce electrical noise.

6. The method of claim 1, wherein said processing the respective intermediate signals comprises:
   determining a peak occurrence in each of the respective intermediate signals; and
   comparing the peak occurrence in each of the respective intermediate signals.

7. The method of claim 1 further comprising:
   correlating the primary vibration signal to an independent secondary vibration signal indicative of snoring by the human patient.

8. The method of claim 7, wherein the independent secondary vibration signal is a filtered pressure wave generated by a nasal pressure cannula or a vibration signal generated by a snoring microphone.

9. The method of claim 1, wherein the at least two vibratory sensors are placed on the back of the patient's neck.

10. The method of claim 1, wherein the at least two vibratory sensors are placed on a side of the patient's neck.

* * * * *